United States Patent
Munk et al.

(10) Patent No.: US 9,358,336 B2
(45) Date of Patent: Jun. 7, 2016

(54) DRUG DELIVERY DEVICE WITH PISTON PROXIMITY SENSING

(71) Applicant: Novo Nordisk A/S, Bagsvaerd (DK)

(72) Inventors: Jens A. Munk, Oelstykke (DK); Carsten S. Andersen, Valby (DK); Bjorn G. Larsen, Birkeroed (DK); Per E. Holm, Tygelsjoe (SE)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 14/387,558

(22) PCT Filed: Mar. 26, 2013

(86) PCT No.: PCT/EP2013/056417
§ 371 (c)(1),
(2) Date: Sep. 24, 2014

(87) PCT Pub. No.: WO2013/144152
PCT Pub. Date: Oct. 3, 2013

(65) Prior Publication Data
US 2015/0080790 A1    Mar. 19, 2015

Related U.S. Application Data

(60) Provisional application No. 61/618,104, filed on Mar. 30, 2012.

(30) Foreign Application Priority Data

Mar. 27, 2012   (EP) ..................... 12161387

(51) Int. Cl.
*A61M 5/172*  (2006.01)
*A61M 5/145*  (2006.01)
*A61M 5/20*   (2006.01)

(52) U.S. Cl.
CPC ............. *A61M 5/172* (2013.01); *A61M 5/1456* (2013.01); *A61M 5/14566* (2013.01); *A61M 5/20* (2013.01); *A61M 2205/33* (2013.01); *A61M 2205/3306* (2013.01)

(58) Field of Classification Search
CPC ................. A61M 2205/33; A61M 2205/3306; A61M 5/1456; A61M 5/14566; A61M 5/172; A61M 5/20
See application file for complete search history.

(56) References Cited

U.S. PATENT DOCUMENTS

| 6,514,230 B1 | 2/2003 | Munk et al. |
| 6,958,053 B1 | 10/2005 | Reilly |

(Continued)

FOREIGN PATENT DOCUMENTS

| DE | 202005012194 U1 | 12/2005 |
| EP | 1911479 A1 | 4/2008 |

(Continued)

*Primary Examiner* — Imani Hayman
(74) *Attorney, Agent, or Firm* — Wesley Nicolas (57) ABSTRACT

Drug delivery device with electronically controlled and axially displaceable piston drive member (10) adapted to engage a loaded cartridge piston. The piston drive member is moveable between a proximal loading position in which a cartridge can be received and a distal loaded position in engagement with the piston. A proximity sensor (11,12) provides a varying output indicative of a varying distance between the piston drive member and the piston. A controller (30) coupled to the proximity sensor is configured to control movement of the piston drive member from the loading position to the loaded position and stop movement when the controller based on input from the proximity sensor system determines that the loaded position has just been reached. By this arrangement it is prevented that a drug-filled cartridge is pressurized during the loading and initializing procedure.

11 Claims, 3 Drawing Sheets

(56) References Cited

U.S. PATENT DOCUMENTS

| | | |
|---|---|---|
| 7,193,521 B2 | 3/2007 | Moberg et al. |
| 7,462,166 B2 | 12/2008 | Cowan et al. |
| 2002/0165491 A1* | 11/2002 | Reilly .......................... 604/154 |
| 2004/0158205 A1 | 8/2004 | Savage |
| 2011/0240836 A1 | 10/2011 | Phan Le |
| 2011/0266446 A1 | 11/2011 | Chang et al. |
| 2011/0306927 A1 | 12/2011 | Watanabe et al. |

FOREIGN PATENT DOCUMENTS

| | | |
|---|---|---|
| WO | 0137905 A2 | 5/2001 |
| WO | 02081011 A1 | 10/2002 |
| WO | 02083209 A1 | 10/2002 |
| WO | 2007094833 A1 | 8/2007 |
| WO | 2009083600 A1 | 7/2009 |
| WO | 2010112376 A1 | 10/2010 |
| WO | 2011032960 A1 | 3/2011 |

* cited by examiner

DRUG DELIVERY DEVICE WITH PISTON PROXIMITY SENSING

CROSS-REFERENCE TO RELATED APPLICATIONS

This application is a 35 U.S.C. §371 National Stage application of International Application PCT/EP2013/056417 (published as WO 2013/144152), filed Mar. 26, 2013, which claimed priority of European Patent Application 12161387.1, filed Mar. 27, 2012; this application claims priority under 35 U.S.C. §119 of U.S. Provisional Application 61/618,104; filed Mar. 30, 2012.

The present invention generally relates to a motorized drug delivery device adapted to receive a drug filled cartridge and subsequently expel a dose therefrom.

BACKGROUND OF THE INVENTION

In the disclosure of the present invention reference is mostly made to the treatment of diabetes, however, this is only an exemplary use of the present invention.

The most common type of durable drug delivery devices adapted to receive a drug filled cartridge and expel a set dose therefrom are driven by manual means or by a spring energized during dose setting, the cartridge being of the type comprising an axially displaceable piston having an initial proximal position. The device may be pen-formed or in the form of a more box-shaped so-called doser. In order to improve convenience, user-friendliness and provide additional features, e.g. detection and storing of expelling data, drug delivery devices have been provided with electrically driven means, typically in the form of an electronically controlled motor driving a piston rod through a gear arrangement, e.g. as shown in U.S. Pat. No. 6,514,230 and US 2011/306927. The same arrangement is also used in infusion pumps, e.g. as shown in U.S. Pat. No. 7,193,521. When a new cartridge is loaded into a motor-driven drug delivery device the piston is first moved proximally allowing a full cartridge to be inserted after which the piston rod is moved into contact with the cartridge piston to bring the drug delivery device in an operational state. The loading of a new cartridge may be performed manually, i.e. the user actuates buttons moving the piston rod back and forth, or it may be partly or fully automated, e.g. the device detects that a cartridge cover is opened and moves back the piston rod, this allowing the user to remove the used cartridge, insert a new and close the cover. When the device detects that the cover has been closed and a cartridge is inserted the piston rod is automatically advanced into engagement with the piston where after the device is ready for use or further initial operations, e.g. a user operated air shot to drive out air in the cartridge or an attached needle.

As the piston in a new cartridge due to manufacturing tolerances is not located at the exact same position, just as a user may also insert a partly used cartridge, the piston rod cannot be automatically advanced to a fixed position but have to be forwarded until engagement with the piston is detected by the motor controller. In the past it has been proposed to detect piston engagement by directly or indirectly detect pressure-build up in the system. For example, when the piston rod engages the piston the resistance to movement will increase and the electric current to the motor will in many control systems increase which can then be detected and used to determine piston engagement, however, this method has a number of drawbacks. As the motor does not stop immediately the cartridge will be pressurized which will subsequently result in an undesired flow of drug when a needle is connected to the cartridge. This can be somewhat compensated by increasing the sensitivity of the current sensing system, but the more sensitive the higher the risk that a false detection occurs because of the variation in the motor current caused by variation in mechanical friction in the motor/gear components. WO 01/37905 discloses an arrangement using a light source and a light sensor arranged on a piston driver to detect when the piston driver has been forwarded into contact with a piston, this resulting in a delay when stopping the motor. Undesired pressurization may also be mitigated by moving back the piston rod slightly, however, it may either be moved too little or too much backwards. A further problem arises when a needle has been connected before the piston rod is advanced as this reduces the pressure build, often to an extent that piston engagement cannot be detected due to a low signal-to-noise ratio. Whether or not engagement is detected with a delay or not at all, the result is an undesired flow of drug. Alternative pressure build up in the system could be detected by incorporating a dedicated sensor, e.g. a strain gauge attached to a component which will be deformed, however, such a system will typically also suffer from a delay in sensing.

Having regard to the above, it is an object of the present invention to provide a motorized drug delivery device adapted to receive a drug-filled cartridge, and in which a piston drive member can be moved automatically into engagement with a cartridge piston in a simple and convenient way, the arrangement being user-friendly, cost-effective as well as reliable. Engagement should be achieved with only a minimum of pressure build-up.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect of the invention a drug delivery device is provided comprising means adapted to receive a cartridge in a loaded position, the cartridge comprising a body portion, a distal outlet portion and an axially displaceable piston with a proximal portion, and an electronically controlled expelling assembly comprising an axially displaceable piston drive member adapted to engage the proximal piston portion of a loaded cartridge, the piston drive member being moveable between a proximal loading position and a distal loaded position in engagement with the proximal piston portion. The device is further provided with a proximity sensor system adapted to provide a varying output indicative of a varying distance between the piston drive member and the proximal piston portion, and a controller coupled to the proximity sensor system and the expelling assembly and configured to control the expelling assembly to move the piston drive member from the loading position to the loaded position and stop movement when the controller based on input from the proximity sensor system determines that the loaded position has just been reached.

By this arrangement it is prevented that a drug-filled cartridge is pressurized during the loading and initializing procedure. The arrangement also allows the position of the piston drive member to be adjusted "on the fly" during normal operation. This would address the problem that after the cartridge loading procedure has been finalized contact between the piston and the piston drive member may be lost due to e.g. external influence such as the device being dropped on a floor. For example, each time the device is turned on a start-up procedure may either check that the piston drive member is in contact with the piston and if necessary adjust the position or, alternatively, move the drive member out of engagement and then subsequently into engagement again. The controller may be in the form of a CPU or a microcontroller as well as their supporting components or any other configuration of electronic components suitable for the described functionality.

It should be noted that the term "engagement" in the context of the present invention and having relation to a cartridge piston and a piston drive member covers situations in which the two structures are in actual contact with each other as well as in near-contact. The term "near-contact" denotes that the piston drive member is advanced to a pre-defined level of proximity to the piston which for all practical purposes corresponds to actual contact. For example, a near-contact condition could be defined as a distance, e.g. 0.2 mm, 0.1 mm or 0.05 mm, an amount of drug in a given cartridge, e.g. 0.1 IU or 0.2 IU of insulin, or a given sensor value, e.g. absolute or a percentage of a measured maximum during the initialization procedure. In the same way the term "just" covers situations in which the two structures are in actual contact but the piston drive member has been advanced slightly further such that the a minimal pressure build-up may have been generated in the cartridge. Engagement could also be provided by using the proximity detection system in a two-step "hybrid" set-up in which information from the proximity sensor system is used to first position the piston rod at a predetermined distance from the piston after which the controller will advance the drive member the remaining known distance.

The controller may be configured to control the expelling assembly to move the piston drive member at a varying speed corresponding to the varying output provided by the proximity sensor system, this allowing a given speed of the piston drive member to be reduced as it approaches the proximal piston portion. The speed may be varied in different ways. For example, at a given sensor system output corresponding e.g. to a distance of approximately 5 mm, the speed may be lowered in a single step or ramped down in a number of steps or continuously such that the piston drive member engages the piston at a reduced speed. The most appropriate solution will be influenced by properties such as the initial speed at which the drive member is moved towards the piston and how finely and fast the speed is controlled by the controller. Alternatively, the motor driving the drive member may be fully stopped when the sensor system output indicates that the drive member is in close proximity to the piston, e.g. 0.25 mm, the inertia of the system providing that the drive member will move into engagement with the piston.

In exemplary embodiments at least a part of the proximity sensor system may be coupled to and move with the piston drive member. For example, the drug delivery device may comprise a first light source providing a light directed at least in part against the proximal piston portion of a loaded cartridge, and a light sensor coupled to the piston drive member and adapted to measure light from the first light source reflected from the proximal piston portion of a loaded cartridge. In such a set-up the first light source and the light sensor provide at least in part a proximity sensor system adapted to provide an output indicative of the distance between the proximal piston portion and the piston drive member. Also the first light source may be coupled to and move with the piston drive member. In addition, light barrier means may be associated with the light sensor and adapted to block or reduce light from reaching the light sensor when the piston drive member has been moved into engagement with the proximal piston portion.

The controller may be configured to determine a first condition in which the piston drive member and the proximal piston portion of a loaded cartridge are at a loading distance from each other corresponding to the loading position of the piston drive member and in which a low level of reflected light is directed to and measured by the light sensor, determine a second condition in which the piston drive member and the proximal piston portion of a loaded cartridge are at an intermediate distance from each other corresponding to an intermediate position of the piston drive member and in which an intermediate level of reflected light is directed to and measured by the light sensor, and determine a third condition in which the piston drive member and the proximal piston portion of a loaded cartridge are in engagement with each other corresponding to the loaded position of the piston drive member and in which a low level of reflected light is directed to and measured by the light sensor. The second condition may be determined as one of many intermediate conditions based on a plurality of measured levels of light or a continuous measurement of a light level. Based at least in part on input from the light sensor, the controller may be further adapted to control the expelling assembly to move the piston drive member from the loading position, through the intermediate position to the loaded position, and stop movement when the loaded position has been reached. For example, the detection of the loading position may be based on additional inputs, e.g. direct or indirect detection of absolute position.

In alternative embodiments the drug delivery device may comprise a second light source arranged stationary relative to the piston drive member and providing backlight, wherein the light sensor is adapted to also measure backlight from the second light source. In such a setup the controller may be configured to determine a first condition in which the piston drive member and the proximal piston portion of a loaded cartridge are at a loading distance from each other corresponding to the loading position of the piston drive member and in which a high level of backlight and a low level of reflected light are directed to and measured by the light sensor, determine a second condition in which the piston drive member and the proximal piston portion of a loaded cartridge are at an intermediate distance from each other corresponding to an intermediate position of the piston drive member and in which an intermediate level of backlight and an intermediate level of reflected light are directed to and measured by the light sensor, and determine a third condition in which the piston drive member and the proximal piston portion of a loaded cartridge are in engagement with each other corresponding to the loaded position of the piston drive member and in which a low level of backlight and a low level of reflected light are directed to and measured by the light sensor. The second condition may be determined as one of many intermediate conditions based on a plurality of measured levels of light or a continuous measurement of a light level. Based at least in part on input from the light sensor, the controller may be further adapted to control the expelling assembly to move the piston drive member from the loading position, through the intermediate position to the loaded position, and stop movement when the loaded position has been reached. Alternatively, the system may be adapted to detect the defined positions using ambient light, e.g. as supplied by sunlight or a lamp.

The piston drive member may be moved at a first speed between the loading and intermediate position, and be moved at a second lower speed between the intermediate and the loaded position. Further speeds as well as continuously varying speeds may be used. The first light source may emit a first type of light, e.g. IR light from a LED, and the second light source may emit a second type of light, e.g. visible light from a white LED. A light source may comprise a light conductor for conducting light to a point of exit.

In the drug delivery devices described above the controller, after the loaded position has been reached, may be adapted to be set to axially move the piston drive element a given distance to thereby expel an amount of drug from a loaded cartridge. The piston drive element may be the in the form of a flexible or rigid piston rod which may be provided with an additional distal piston washer or foot element to improve contact with a proximal piston surface of a loaded cartridge. The sensor and first light source may be arranged on the distal-most portion of the rod or foot, e.g. in a central cavity, the necessary conductors being guided in a hollow piston rod or formed integrally therewith.

In addition to the described proximity sensor system the drug delivery device may in addition be equipped with a traditional pressure based detection system, e.g. detecting piston contact during a cartridge loading procedure based on measured variations in motor current. Such an additional system may also provide a back-up in case a cartridge is inserted in which the piston does not have the required reflecting properties. Alternatively, an inserted cartridge's failure to reflect light may also be detected by analysing the measured values, e.g. the level or variation of reflected light measured as a function of piston rod advancement may be outside pre-set limits for the detection of a proper cartridge having been inserted.

The drug delivery device as described above may be provided in combination with a drug-filled cartridge comprising an axially displaceable piston having a proximal portion, the proximal portion comprising a surface adapted to reflect light as well as an engagement portion adapted to engage the piston drive member.

In a second aspect of the invention a proximity detection system is provided comprising a first and a second element movable relative to each other, the second element comprising a reflecting surface adapted to reflect light, a first light source coupled to and moving with the first element and providing a light directed at least in part against the reflecting surface, and a second light source not moving with the first element and providing backlight. A light sensor is coupled to the first element and adapted to measure light from the first light source reflected from the reflecting surface as well as backlight from the second light source, light barrier means is associated with the light sensor and adapted to block light from reaching the light sensor when the first and second element have been moved into engagement with each other, and a controller is coupled to the light sensor. The controller is configured to determine a first condition in which the first and second elements are at a first distance from each other and in which a high level of backlight and a low level of reflected light are directed to and measured by the light sensor, a second condition in which the first and second elements are at an intermediate distance from each other and in which an intermediate level of backlight and an intermediate level of reflected light are directed to and measured by the light sensor, and a third condition in which the first and second elements are in engagement with each other and in which a low level of backlight and a low level of reflected light are directed to and measured by the light sensor. By providing an additional backlight failsafe detection of system conditions is improved. The first light source may emit a first type of light and the second light source may emit a second type of light.

The proximity detection system may further comprise a drug-filled cartridge comprising an axially displaceable piston forming the second element, means for holding the cartridge in a loaded position, and drug expelling means adapted to axially move the first element from a first position corresponding to the first condition, through an intermediate position corresponding to the second condition, to an engagement position corresponding to the third condition, wherein the controller is configured to control the drug expelling means to move the first element from the first position, through the intermediate position to the engagement position, and stop movement when the engagement position has been reached. The controller may, after the engagement position has been reached, be set to axially move the first element a given distance to thereby expel an amount of drug from the cartridge.

In a further aspect of the invention a drug delivery device is provided comprising a compartment adapted to receive a drug-filled cartridge in a loaded position, the cartridge comprising a distal outlet portion and an axially displaceable piston, an electronically controlled expelling assembly comprising an axially displaceable piston drive member adapted to move the piston of a loaded cartridge from a start-of-dose position to an end-of-dose position to thereby expel a given dose, and electronically controlled signal means. When a cartridge is loaded the combined cartridge and expelling assembly will have elastic properties, whereby a pressure is build up in the cartridge when the piston drive member has reached the end-of-dose position, this resulting in a flow of drug from the distal outlet for a period of time after the piston drive member has reached the end-of-dose position. Correspondingly, the signal means is controlled to produce a signal during movement of the piston drive member between the start-of-dose and the end-of-dose position, as well as for a period of time after the piston drive member has reached the end-of-dose position. By this arrangement the waiting period until the pressure has been reduced and the (almost) full amount of drug has been expelled is perceived as part of the whole injection and not an extra annoyance. The period of time may be pre-determined or the period of time may be calculated based on measuring a value indicative of the pressure in the cartridge. The signal means may produce one of an audible, tactile or visual signal.

In an exemplary embodiment the signal means produces at least one of an audible or a tactile signal, the expelling assembly produces at least one of an audible or a tactile signal (or "noise") during expelling of a dose of drug, wherein the signal means is controlled to produce a signal which is not identical during the period before and after the piston drive member has reached the end-of-dose position, thereby producing a combined signal which is perceived by a user as near-constant during both periods.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs, this including analogues thereof as well as combinations with one or more other drugs.

BRIEF DESCRIPTION OF THE DRAWINGS

In the following exemplary embodiments of the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

An exemplary embodiment of the invention is implemented in an electronically controlled motorized drug delivery device adapted to receive a drug-filled cylindrical cartridge comprising an outlet and an axially displaceable piston, the device comprising a housing, a compartment adapted to receive and hold a cartridge, an electronically controlled expelling assembly comprising an axially displaceable piston drive member adapted to engage the piston of a loaded cartridge, a controller coupled to the expelling assembly and configured to control the expelling assembly to move the piston in a distal direction to thereby expel drug from a loaded cartridge, an electrical energy source for the controller and the expelling assembly, as well as user-operated input means for setting a desired dose of drug to be expelled. Such a drug delivery device is known per se, e.g. in the form of a compact doser incorporating a flexible piston rod as disclosed in U.S. Pat. No. 6,514,230, a pen-formed device incorporating a rigid piston rod as disclosed in US 2011/306927 or an infusion pump as disclosed in U.S. Pat. No. 7,193,521 which are all hereby incorporated by reference.

As also described initially, a motorized drug delivery device is adapted to have an empty cartridge replaced with a new cartridge in which course the piston rod is normally moved proximally to a loading position by the motorized expelling assembly, which action may be activated by e.g. a cover being opened or a button being pressed. Correspondingly, when a new cartridge has been inserted the piston rod is normally moved automatically distally to a loaded position in contact with the piston by the motorized expelling assembly, which action may be activated by a cover being closed or a button being pressed. The device may further be provided with means for detecting that a cartridge has been loaded to prevent an initialization procedure when no cartridge is mounted.

Figure 1:
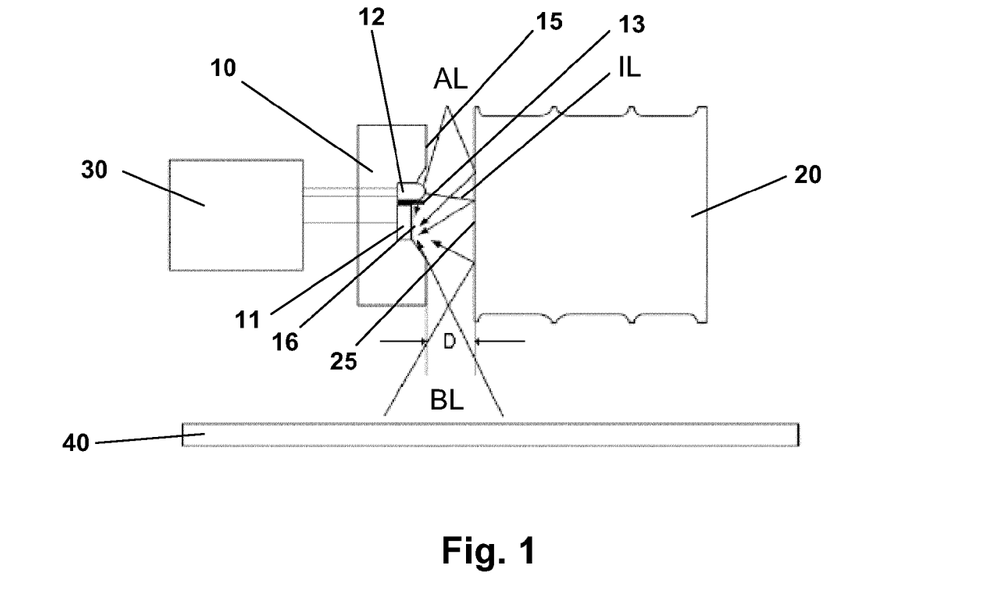
FIG. 1 shows schematically components of a drug delivery device in a loading state.

Referring to FIG. 1 a schematic representation of components of a drug delivery device is shown, the figure only showing those structures relevant for illustrating an embodiment of the invention. More specifically, the drug delivery device comprises a piston drive member in the form of a piston rod washer 10 mounted on a piston rod (not shown) and driven by an electronically controlled motorized mechanism (not shown), a piston 20 mounted in a cartridge (not shown), and a controller 30. The piston rod washer comprises a distal surface 15 adapted to engage a proximal surface 25 on the piston, the distal surface being provided with a central cavity 16 in which a light sensor 11 and a first light source 12 in the form of a IR LED are arranged next to each other with a barrier member 13 being mounted there between. The IR LED is arranged to direct IR light IL towards the proximal surface of the piston and the light sensor is arranged to detect the reflected light therefrom, the barrier preventing direct light from the IR LED to reach the sensor. The device is further provided with a backlight 40, e.g. a white LED, which is used to both securely determine the position of the sensor relative to the piston and allow the user to inspect the cartridge. Light may be provided directly by the source or indirectly via e.g. a light conductor.

Figure 2:
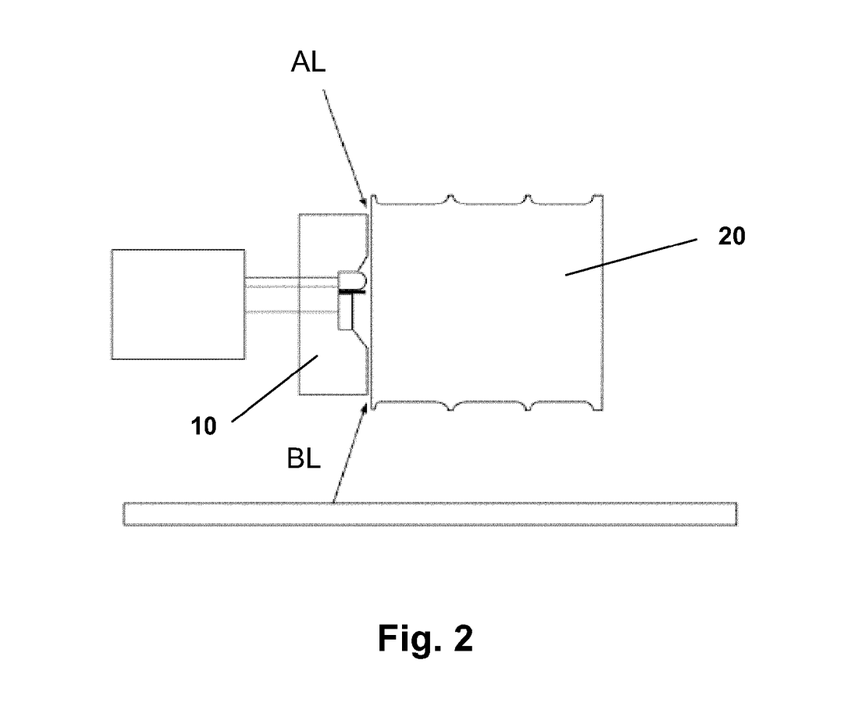
FIG. 2 shows the drug delivery device in a loaded state.

In FIG. 1 the piston rod washer has been advanced to a distance D corresponding to approximately 2 mm from the piston, this allowing both reflected IR light and backlight BL (as well as ambient light AL) to reach the sensor. In FIG. 2 the piston rod washer has been further advanced and is now in contact (or near-contact) with the piston preventing (or almost preventing) both reflected IR light, ambient light and backlight from reaching the sensor, this indicating that contact (or near-contact) and thereby engagement has been established between the piston drive member and the piston.

Figure 3:
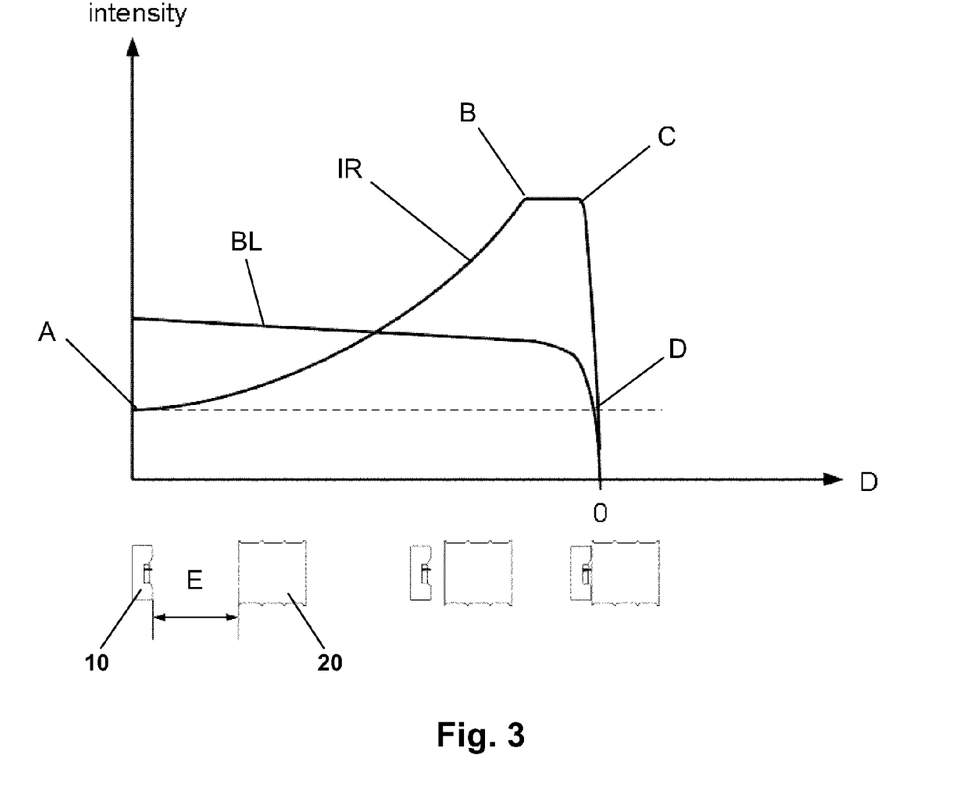
FIG. 3 illustrates a detection principle for a proximity detection system.

FIG. 3 illustrates a possible detection principle for a proximity detection system provided with a backlight. Position A corresponds to the piston rod being positioned in its loading position at a distance E from the piston of a loaded cartridge in which position a high level of backlight BL (as well as ambient light) reaches the sensor whereas the level of reflected IR light from the piston proximal surface is low. As the piston rod washer is advanced towards the piston the level of reflected light rises whereas the level of sensed backlight initially is almost constant, this indicating that the sensor and thus the piston rod washer is approaching the piston but is still relatively far therefrom, this allowing the piston rod to be advanced quickly. In the shown embodiment the sensor and light system is designed to reach a saturation level in position B in which the output from the sensor flattens when it has arrived at a given short distance from a loaded piston, e.g. 2 mm. The piston rod is now slowly advanced until the reflected light starts dropping quickly after position C. At that point, the distance is below a few tenth of a millimetre. Advancing the piston rod further (which may be at a further reduced speed) is stopped when the reflected IR light has reached a given stop level where most (as in position D) or all of the light is blocked. The stop level may be defined as an absolute percentage for the sensor output or a percentage of the maximum measured value which in FIG. 3 is 100%. The barrier between the IR emitter and the light sensor secures that no false light escapes to the sensor. Since it is not possible to distinguish between the two situations where the reflected IR levels are identical (A and D in FIG. 3) the backlight (and ambient light) level may be measured as well. The backlight will also decrease rapidly so combining the two signals will further enhance the detection liability. Alternative, the backlight may be dispensed with and the system may rely on ambient light only which, indeed, would require that the system is used under conditions with a certain level of ambient light.

Instead of using ambient or backlight to discriminate between position A and D it would be possible to determine the absolute position of the piston rod, e.g. by moving the piston rod fully proximally, this establishing a loading position A.

Figure 4:
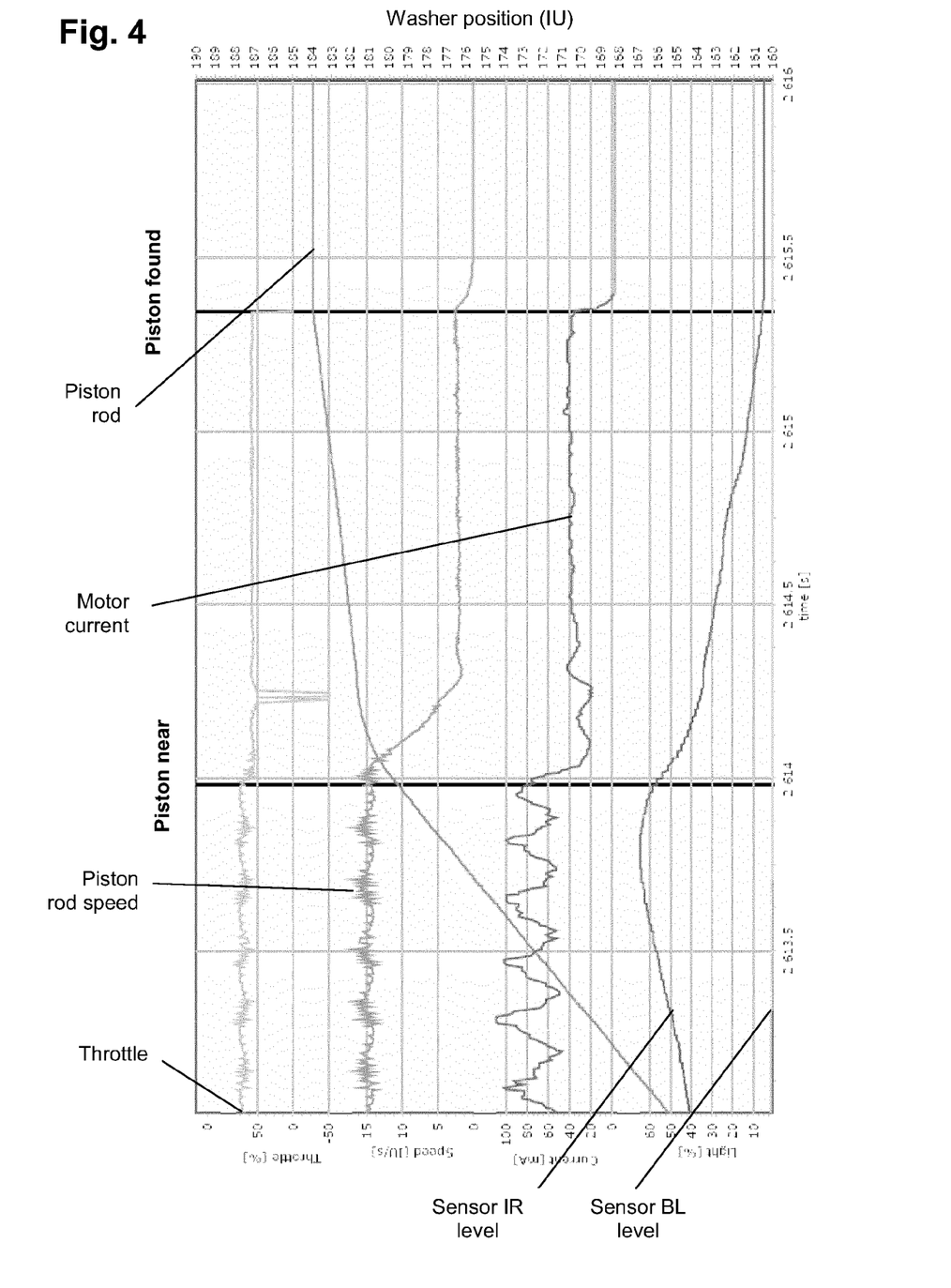
FIG. 4 shows data for a set-up similar to the system shown in FIG. 3.

FIG. 4 shows experimental data for a set-up similar to the system shown in FIG. 3. Two states are indicated: "Piston near" and "piston found", the former corresponding to a pre-set level of detected light and the latter corresponding to engagement between the piston drive member and the cartridge piston. The piston rod washer position is measured in IU corresponding to a standard 3 ml 100 IU/ml Novo Nordisk Penfill® insulin cartridge with zero corresponding to a loading position in which the piston is positioned in its proximal-most position. The figure shows that until the "piston near" state has been reached the motor is controlled at high throttle resulting in corresponding high motor current and piston rod speed of around 15 IU/s. When the "piston near" state at a pre-defined decreasing light level (either absolute or relative) has been reached the throttle and corresponding current and speed are lowered. At this position the distance between the piston rod washer and the piston corresponds to approximately 15 IU. As appears, the sensor in this set-up does not reach a saturation level as shown in FIG. 3. The motor is then throttled down to move at a speed of 2-3 IU/s until the IR level is below a pre-defined level of 3% corresponding to the "piston found" state. The piston rod washer is now as close as possible (less than 0.5 IU in the shown embodiment) to the piston without touching it. For all practical purposes this "near-contact" level of engagement is fully acceptable.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device comprising:
   a compartment adapted to receive a cartridge in a loaded position, the cartridge comprising a body portion, a distal outlet portion and an axially displaceable piston with a proximal portion,
   an electronically controlled expelling assembly comprising an axially displaceable piston drive member adapted to engage the proximal piston portion of the cartridge, the piston drive member being moveable between a proximal loading position and a distal loaded position in engagement with the proximal piston portion,
   a proximity sensor system adapted to provide a varying output indicative of a varying distance between the piston drive member and the proximal piston portion,
   a first light source providing a light directed at least in part against the proximal piston portion of the cartridge,
   a light sensor coupled to the piston drive member and adapted to measure light from the first light source reflected from the proximal piston portion of the cartridge,
   whereby the first light source and the light sensor provide at least in part a proximity sensor system adapted to provide an output indicative of the distance between the proximal piston portion and the piston drive member
   a controller coupled to the proximity sensor system and the expelling assembly and configured to control the expelling assembly to move the piston drive member from the loading position to the loaded position and stop movement when the controller based on input from the proximity sensor system determines that the loaded position has just been reached,
   the controller further configured to:
   determine a first condition in which the piston drive member and the proximal piston portion of the cartridge are at a loading distance from each other corresponding to the loading position of the piston drive member and in which a low level of reflected light is directed to and measured by the light sensor,
   determine a second condition in which the piston drive member and the proximal piston portion of the cartridge are at an intermediate distance from each other corresponding to an intermediate position of the piston drive member and in which an intermediate level of reflected light is directed to and measured by the light sensor,
   determine a third condition in which the piston drive member and the proximal piston portion of the cartridge are in engagement with each other corresponding to the loaded position of the piston drive member and in which a low level of reflected light is directed to and measured by the light sensor, and
   control the expelling assembly to move the piston drive member from the loading position, through the intermediate position to the loaded position, and stop movement when the loaded position has been reached.

2. The drug delivery device as in claim 1, wherein at least a part of the proximity sensor system is coupled to and moves with the piston drive member.

3. The drug delivery device as in claim 1, wherein the first light source is coupled to and moves with the piston drive member.

4. The drug delivery device as in claim 1, further comprising:
   a light barrier structure associated with the light sensor and adapted to block or reduce light from reaching the light sensor when the piston drive member has been moved into engagement with the proximal piston portion.

5. The drug delivery device as in claim 1, wherein the controller is configured to control the expelling assembly to move the piston drive member at a varying speed corresponding to the varying output provided by the proximity sensor system, this allowing a given speed of the piston drive member to be reduced as it approaches the proximal piston portion.

6. The drug delivery device as in claim 1, further comprising:
   a second light source arranged stationary relative to the piston drive member and providing backlight,
   wherein the light sensor is adapted to also measure backlight from the second light source, and
   wherein the controller is configured to:
   determine a first condition in which the piston drive member and the proximal piston portion of the cartridge are at a loading distance from each other corresponding to the loading position of the piston drive member and in which a high level of backlight and a low level of reflected light are directed to and measured by the light sensor,
   determine a second condition in which the piston drive member and the proximal piston portion of the cartridge are at an intermediate distance from each other corresponding to an intermediate position of the piston drive member and in which an intermediate level of backlight and an intermediate level of reflected light are directed to and measured by the light sensor,
   determine a third condition in which the piston drive member and the proximal piston portion of the cartridge are in engagement with each other corresponding to the loaded position of the piston drive member and in which a low level of backlight and a low level of reflected light are directed to and measured by the light sensor, and
   control the expelling assembly to move the piston drive member from the loading position, through the intermediate position to the loaded position, and stop movement when the loaded position has been reached.

7. The drug delivery device as in claim 1, wherein the piston drive member is moved at a first speed between the loading and intermediate position, and is moved at a second lower speed between the intermediate and the loaded position.

8. The drug delivery device as in claim 6, wherein the first light source emits a first type of light and the second light source emits a second type of light.

9. The drug delivery device as in claim 1, wherein the controller, after the loaded position has been reached, is adapted to be set to axially move the piston drive element a given distance to thereby expel an amount of drug from the cartridge.

10. The drug delivery device as in claim 1, in combination with:
- a drug-filled cartridge comprising an axially displaceable piston having a proximal portion, the proximal portion comprising a surface adapted to reflect light as well as an engagement portion adapted to engage the piston drive member.

11. A drug delivery device comprising:
- a compartment adapted to receive a cartridge in a loaded position cartridge, the cartridge comprising a body portion, a distal outlet portion and an axially displaceable piston with a proximal portion,
- an electronically controlled expelling assembly comprising an axially displaceable piston drive member adapted to engage the proximal piston portion of the cartridge, the piston drive member being moveable between a proximal loading position and a distal loaded position in engagement with the proximal piston portion,
- a proximity sensor system adapted to provide a varying output indicative of a varying distance between the piston drive member and the proximal piston portion,
- a first light source providing a light directed at least in part against the proximal piston portion of the cartridge,
- a second light source arranged stationary relative to the piston drive member and providing backlight,
- a light sensor coupled to the piston drive member and adapted to measure light from the first light source reflected from the proximal piston portion of the cartridge,
- whereby the first light source and the light sensor provide at least in part a proximity sensor system adapted to provide an output indicative of the distance between the proximal piston portion and the piston drive member, and
- wherein the light sensor is adapted to also measure backlight from the second light source,
- a controller coupled to the proximity sensor system and the expelling assembly and configured to control the expelling assembly to move the piston drive member from the loading position to the loaded position and stop movement when the controller based on input from the proximity sensor system determines that the loaded position has just been reached,
- wherein the controller is configured to:
- determine a first condition in which the piston drive member and the proximal piston portion of the cartridge are at a loading distance from each other corresponding to the loading position of the piston drive member and in which a high level of backlight and a low level of reflected light are directed to and measured by the light sensor,
- determine a second condition in which the piston drive member and the proximal piston portion of the cartridge are at an intermediate distance from each other corresponding to an intermediate position of the piston drive member and in which an intermediate level of backlight and an intermediate level of reflected light are directed to and measured by the light sensor,
- determine a third condition in which the piston drive member and the proximal piston portion of the cartridge are in engagement with each other corresponding to the loaded position of the piston drive member and in which a low level of backlight and a low level of reflected light are directed to and measured by the light sensor, and
- control the expelling assembly to move the piston drive member from the loading position, through the intermediate position to the loaded position, and stop movement when the loaded position has been reached.

* * * * *